(12) United States Patent
He

(10) Patent No.: US 10,416,102 B2
(45) Date of Patent: Sep. 17, 2019

(54) X-RAY DIFFRACTION DEVICE AND METHOD TO MEASURE STRESS WITH 2D DETECTOR AND SINGLE SAMPLE TILT

(71) Applicant: Bruker AXS, Inc., Madison, WI (US)

(72) Inventor: Bob Baoping He, Hercules, CA (US)

(*) Notice: Subject to any disclaimer, the term of this patent is extended or adjusted under 35 U.S.C. 154(b) by 272 days.

(21) Appl. No.: 15/631,533

(22) Filed: Jun. 23, 2017

(65) Prior Publication Data

US 2018/0372658 A1   Dec. 27, 2018

(51) Int. Cl.
| G01N 23/20 | (2018.01) |
| G01N 23/207 | (2018.01) |
| G01N 23/20025 | (2018.01) |
| G01N 23/20016 | (2018.01) |
| G01N 23/2055 | (2018.01) |

(52) U.S. Cl.
CPC ..... G01N 23/207 (2013.01); G01N 23/20016 (2013.01); G01N 23/20025 (2013.01); G01N 23/2055 (2013.01); G01N 2223/3306 (2013.01); G01N 2223/607 (2013.01); G01N 2223/61 (2013.01)

(58) Field of Classification Search
CPC ........... G01N 23/207; G01N 23/20016; G01N 23/20025; G01N 23/2055; G01N 2223/607; G01N 2223/61; G01N 2223/3306
See application file for complete search history.

(56) References Cited

U.S. PATENT DOCUMENTS

| 7,035,373 B2 | 4/2006 | Omote |
| 8,855,266 B2 * | 10/2014 | Yasukawa ............ G01N 23/207 378/63 |
| 9,372,163 B2 | 6/2016 | Ruf et al. |

(Continued)

FOREIGN PATENT DOCUMENTS

| EP | 2940461 A1 * | 11/2015 | ....... G01N 23/20016 |
| JP | 11281595 A | 10/1999 | |

(Continued)

OTHER PUBLICATIONS

He, Bob B., "Measurement of Residual Stresses in Thin Films by Two-Dimensional XRD", Materials Science Forum, vol. 524-525., Sep. 2006.

(Continued)

*Primary Examiner* — Kiho Kim
(74) *Attorney, Agent, or Firm* — Benoit & Côté Inc.

(57) ABSTRACT

A method is provided for performing an X-ray diffraction stress analysis of a sample such as a thin film, a coating, or a polymer. The sample has a surface with two perpendicular axes $S_1$, $S_2$ within a plane of the surface, and a third axis $S_3$ perpendicular to the sample surface plane. An X-ray beam is directed at the sample surface at a relatively low angle with regard to the surface plane. X-ray energy is diffracted from the sample and detected with a two-dimensional X-ray detector at a plurality of rotational orientations of the sample about $S_3$. The third axis $S_3$ is maintained at a constant tilt angle during the entire X-ray diffraction stress analysis, thereby avoiding the significant error associated to the movement of a cradle track of a goniometer used for the X-ray diffraction stress analysis and on which measurements at a low 2θ angle are highly sensitive.

23 Claims, 7 Drawing Sheets

(56) References Cited

U.S. PATENT DOCUMENTS

| | | | |
|---|---|---|---|
| 10,247,683 B2* | 4/2019 | Yun | G01N 23/223 |
| 2003/0012335 A1 | 1/2003 | Yokoyama | |
| 2009/0034681 A1* | 2/2009 | Je | G01N 23/046 |
| | | | 378/74 |
| 2015/0012239 A1 | 1/2015 | Ishibashi | |
| 2017/0082561 A1* | 3/2017 | Yasukawa | G01N 23/207 |
| 2017/0343491 A1* | 11/2017 | Borna Tutuc | G01N 23/207 |

FOREIGN PATENT DOCUMENTS

| | | |
|---|---|---|
| JP | 2005257306 A | 9/2005 |
| JP | 201511024 A | 1/2015 |
| JP | 2017504044 A | 2/2017 |
| KR | 100827392 B1 | 10/2004 |
| WO | 2007052688 A1 | 5/2007 |

OTHER PUBLICATIONS

He, Bob, B., "Two-Dimensional X-Ray Diffraction", pp. 249-326, Nov. 12, 2009.

* cited by examiner

X-RAY DIFFRACTION DEVICE AND METHOD TO MEASURE STRESS WITH 2D DETECTOR AND SINGLE SAMPLE TILT

BACKGROUND OF THE INVENTION

Field of the Invention

This invention relates generally to the field of X-ray diffraction and, more specifically, to the stress measurement of surfaces using 2D X-ray diffraction.

Description of the Related Art

In the field of X-ray diffraction, radiation with a wavelength $\lambda$ in the subnanometer range is directed to a sample of a crystalline material with a given interatomic spacing, d. When the angle of incidence, $\theta$, relative to the crystalline structure satisfies the Bragg equation, $\lambda=2d \sin \theta$, an interferometrically reinforced signal (the diffracted signal), may be observed leaving the material, with an angle of emission being equal to an angle of incidence. Both angles are measured with respect to a direction normal to the interatomic spacing of interest, hence the angle between the incident radiation and the diffraction radiation amounts to $2\theta$ when the angle $\theta$ satisfies the Bragg condition. X-ray energy is diffracted along angles that reside within diffraction cones respecting the Bragg equation and corresponds to different values of interatomic spacing can be observed by positioning a detector at an appropriate angle.

FIG. 1 illustrates an apparatus, namely a goniometer 100, in which a sample may be held and irradiated by an X-ray source 102. In one type of measurement, both the X-ray source 102 and a detector 108 are kept at fixed locations with respect to base 104, while a sample holder 106 is rotated in two dimensions by respective rotation angles $\phi$ and $\psi$ to allow for different incident angles of an X-ray beam with respect to a surface of the sample.

FIG. 2 illustrates diffraction cones that correspond to a sample subject to diffraction as described above. With the X-ray beam directed along an incident angle $\theta$, the sample diffracts X-rays at a corresponding angle $\theta$ if the incident angle satisfies the Bragg condition. For ease of description, the angle of the incident X-ray can be defined as a 0° reference, as shown in FIGS. 2-3, with the diffracted ray energy having an angle $2\theta$ with respect to the 0° reference. A plurality of discrete values of $\theta$ satisfy the Bragg condition for a single incident X-ray beam, hence a plurality of diffraction angles $2\theta$ form a respective plurality of diffraction cones.

FIGS. 2-3 further illustrate that diffraction cones can form in a forward or in a backward direction, and that each of the diffraction cones is characterized by a diffraction angle $2\theta$ that ranges from low to high. A low $2\theta$ measurement is typically defined as a measurement where the diffraction cone of interest (i.e., the one that is collected and analyzed) has a diffraction angle $2\theta<90°$. Conversely, if the diffraction cone of interest during a measurement has a diffraction angle $2\theta>90°$ (or $2\theta>100°$ or $2\theta>120°$ depending on the definition), the measurement is referred to as a high $2\theta$ measurement.

X-ray diffraction can be used for stress measurement of crystalline structures. Mechanical stress can be represented by a stress tensor and, when applied to the material, varies certain interatomic distances in the crystal. As these distances are modified along different directions in the crystal, the angle of diffraction satisfying the Bragg condition changes. This situation results in a deformation of the diffraction cones measured by the detector. This is shown in FIG. 5.

In practice, the stress on the sample may be represented by a tensor, i.e., each orientation in the crystal lattice of the sample has its own independent value for strain, and shearing stresses may also be present. This results in deformations that are not uniform in a given diffraction cone, e.g., the detector may collect diffracted X-ray energy that falls within a ring of an ordinarily circular shape that is enlarged in one direction and/or shrunk in another direction. This, for example, can deform the circle into a "peanut" shape.

By collecting the diffracted X-ray energy with the sample rotated at different orientations along a particular angular direction referred to, in conventional measurement systems, as the "tilt angle" $\psi$, and by comparing the deviation or "shift" in diffraction angle with respect to the expected diffraction angle of an unstressed sample, the stress tensor can be characterized. Determining a stress tensor based on shifts of the diffraction angle $2\theta$ for specific parts of the diffraction cone and for different tilt angles $\psi$ can be done by applying conventional techniques for stress determination, as disclosed, for example, in *Two-Dimensional X-Ray Diffraction* by Bob He, Wiley & Sons, 2009.

FIG. 5 illustrates the relationship between diffraction cones and sample orientation in Eulerian geometry. For simplicity, only two diffraction cones representing forward and backward diffraction, respectively, are shown. The regular diffraction cones (solid lines) are from a sample with no stress, so the $2\theta$ angles are constant at all $\gamma$ angles, where $\gamma$ is an angular position along a circle formed by the intersection of the cone with a plane perpendicular to the incident X-ray beam. $\Delta\gamma$ is the range of all $\gamma$ angles of diffracted rays detectable by the detector. The distorted diffraction rings are from a sample under stress (dotted lines), so the diffraction angle $2\theta$ becomes a function of $\gamma$ and the sample orientation ($\omega$, $\psi$, $\phi$), where $\omega$, $\psi$ and $\phi$ are rotational coordinates that define the sample orientation as shown in FIG. 1.

The fundamental equation for stress measurement of components of the stress tensor a with two-dimensional (2D) X-ray diffraction can be given as:

$$S_1(\sigma_{11}+\sigma_{22}+\sigma_{33})+ \\ \frac{1}{2}S_2(\sigma_{11}h_1^2+\sigma_{22}h_2^2+\sigma_{33}h_3^2+2\sigma_{12}h_1h_2+2\sigma_{13}h_1h_3+2\sigma_{23}h_2h_3)= \\ \ln\left(\frac{\sin\theta_0}{\sin\theta}\right) \quad (1)$$

where $S_1$ and $\frac{1}{2}S_2$ are the macroscopic elastic constants, and $h_1$, $h_2$ and $h_3$ are the three components of the unit diffraction vector expressed in the sample coordinates. The macroscopic elastic constants $S_1$ and $\frac{1}{2} S_2$ are defined in terms of the elasticity constants E (Young's modulus) and v (Poisson's ratio), where $S_1=-v/E$ and $\frac{1}{2} S_2=(1+v)/E$.

For Eulerian geometry, where $h_1$, $h_2$ and $h_3$ are expressed in sample coordinates $S_1S_2S_3$, the three components of the unit diffraction vector are:

$h_1$=sin $\theta$(sin $\phi$ sin $\psi$ sin $\omega$+cos $\phi$ cos $\omega$)+cos $\theta$ cos $\gamma$ sin $\phi$ cos $\psi$−cos $\theta$ sin $\gamma$(sin $\phi$ sin $\psi$ cos $\omega$−cos $\phi$ sin $\omega$)

$h_2$=−sin $\theta$(cos $\phi$ sin $\psi$ sin $\omega$−sin $\phi$ cos $\omega$)−cos $\theta$ cos $\gamma$ cos $\phi$ cos $\psi$+cos $\theta$ sin $\gamma$(cos $\phi$ sin $\psi$ cos $\omega$+sin $\phi$ sin $\omega$)

$$h_3 = \sin\theta \cos\psi \sin\omega - \cos\theta \sin\gamma \cos\psi \cos\omega - \cos\theta \cos\gamma \sin\psi \quad (2)$$

However, as mentioned above, typical detectors are only capable of collecting X-ray energy along an arc of a circle formed by a given diffraction cone. If a stress, represented by a tensor, is applied, each arc of a given circle undergoes a shift that depends on the different tensor components of the stress. The sample is then rotated in different sample orientations so the detector can measure how the shift of the arc of circle of the diffraction cone changes depending on the sample orientation. In practice, this is done by rotating the sample about different axes using the goniometer, where both the detector and X-ray source are kept at their original position. The sample is secured to a rotatable sample holder in the goniometer center and irradiated by the X-ray source. The angular orientation of the sample is then varied by the goniometer, typically to change the angles $\psi$ and $\phi$. A detected shift of the diffraction angle $2\theta$ is assumed to be induced by stress, and is measured in different arcs of the ring corresponding to the intersection of the detector with the diffraction cone of interest for a selected value of $2\theta$.

Thin films, coatings, and polymers are among the samples for which stress characterization may be needed. For example, when a thin film is applied on a substrate, it is likely that the thin film and the substrate have different coefficients of thermal expansion. Therefore, any temperature change occurring after depositing the thin film or annealing is expected to produce residual stress. Since thin films and coatings are thin by definition, the vertical component of the stress, relative to the sample surface (or along the z-axis), is typically negligible. The stress tensor is biaxial and can thus be characterized by five components instead of the usual six: ($\sigma_{11}$, $\sigma_{12}$, $\sigma_{22}$, $\sigma_{13}$, $\sigma_{23}$).

However, measuring stress using X-ray diffraction on thin films, coatings, and polymers remains a challenge due to more significant sensitivity to mechanical errors than with bulkier materials. Moreover, diffraction signals from thin layers are typically weak, their stress or strain gradients are steep, and other imperfections resulting from the thin nature of the coatings can decrease the accuracy of the measurement. For a given material, the X-ray penetration depth is dependent on the incident angle, as shown in FIG. 4. The incident angle is the angle between the incident X-ray beam and the sample surface. The lower the incident angle, the shallower the penetration depth. When residual stresses are measured on a thin film or coating, it is preferable to control the incident angle to keep it low, to get the most X-ray scattering from the thin film layer and not from the underlying substrate, as shown in FIG. 4. In practice, however, this is hard to achieve as low $2\theta$ measurements suffer from serious drawbacks, particularly in relation with the error on the height of the sample.

Conventional methods of X-ray diffraction stress determination are not well suited to determining the stress tensor of thin films where high $2\theta$ diffraction cones are not available or appropriate. Furthermore, conventional methods of stress determination still suffer from the sample height error and require time to perform the measurements. Two conventional methods are described below.

In order to better describe the state of the art, FIG. 6 illustrates the diffraction geometry with a point (0D) detector. The hemisphere represents all the possible orientations from the origin O of the sample coordinates $S_1 S_2 S_3$, where $S_1$ and $S_2$ are on the sample surface, and $S_3$ is the normal to the sample surface. When the Bragg condition is satisfied, the incident beam makes an angle $\theta$ with the sample surface and the diffracted beam makes an angle of $\theta$ with the sample surface on the other side. The diffraction vector H, defined as a unit vector bisecting the incident beam and the diffracted beam, is on the sample normal direction. Its components in the $S_1 S_2$ plane can be traced for a plurality of diffracted beams, hence the trace of diffraction vectors projected onto this plane shown in FIG. 7.

Indeed, in order to measure stress, the diffraction data needs to be collected at several sample orientations. FIG. 7 shows a diffraction vector trace determined with a point detector with the sample at several tilt angles $\psi$. The diffraction vector $H_0$ points to the sample normal direction $S_3$, corresponding to no sample tilt, i.e., tilt angle $\psi=0°$. The diffraction vectors $H_1$, $H_2$ and $H_3$ represent the diffraction vector direction (i.e., defined as bisecting the incident and diffracted beams) corresponding to three tilt angles, for instance $\psi$ angles of 15°, 30° and 45° respectively. The diffraction vectors (e.g., from $H_0$ to $H_3$) point onto a hemisphere of unitary radius having the origin O as a center. The resulting sequence of points on this hemisphere defines a curve in space defined as the trace of diffraction vectors, which can later be projected onto the plane of the sample surface defined by $S_1$ and $S_2$ for analysis.

In order to define a trace of diffraction vectors, a plurality of measurements are usually required, each one for a given tilt angle $\psi$ value. In the prior art, typically, four measurements are taken to define a trace of diffraction vectors. This must be repeated for multiple different values of $\phi$, typically eight. In such a case, the total number of measurements amounts to 32, which requires considerable time to perform.

With a 2D detector, the trace of the diffraction vector covers a range which can be determined from an arc of a circle (i.e., a portion of a ring from the diffraction cone of interest) detected by the detector at a single position of the detector, which is advantageous compared to moving a point detector to multiple locations. FIG. 8 shows two different $\gamma$ planes and their cross sections with a diffraction cone. The $\gamma$ plane is defined as a half plane with the incident beam line (also the axis of the diffraction cone) as the edge. Regardless of the value of $2\theta$, all diffracted beams within a $\gamma$ plane have the same $\gamma$ value. The $\gamma$-plane denoted by $\gamma$ contains the incident beam represented by a vector $S_o$, the diffracted beam represented by a vector $S$ and the diffraction vector H. The $\gamma$-plane denoted by $\gamma'$ contains the incident beam vector $S_o$, the diffracted beam vector $S'$ and the diffraction vector H'. The two vectors H and H' represent the two extremes of the diffraction vector distribution of the diffraction ring within the $\gamma$ range, $\Delta\gamma$. Therefore, FIG. 8 illustrates the angular range $\Delta\gamma$ that the detector must cover to determine two different diffraction vectors H and H'. The angle between the two diffraction vectors is given by $$\Delta\psi = 2 \arcsin(\cos\theta \sin(\Delta\gamma/2)) \quad (3)$$

The method with the 2D detector suffers from similar drawbacks as the point detector, namely, sample height errors that increase with low $2\theta$ measurements. Moreover, both methods are time-consuming since both angles $\psi$ and $\phi$ must be changed multiple times (e.g., 4 and 8 times, respectively, for a total of 32 measurements).

SUMMARY OF THE INVENTION

In accordance with the present invention, there is provided a method for performing an X-ray diffraction stress analysis of a sample. The sample can be a thin film, a coating, or a polymer. The sample has a surface with two perpendicular axes $S_1$, $S_2$ within a plane of the surface, a third axis $S_3$ being perpendicular to the sample surface plane.

The method comprises directing an X-ray beam at the sample surface at an angle relative to the surface plane (i.e., the incident angle). This can be performed in a goniometer setting. In a measurement, X-ray energy is diffracted from the sample and detected with a two-dimensional X-ray detector. It is detected at a relatively low 2θ. The measurements are performed at a plurality of rotational orientations of the sample about $S_3$, the third axis $S_3$ being maintained at a constant tilt angle ψ during the entire X-ray diffraction stress analysis. The tilt angle ψ is the angle of $S_3$ the normal to the sample surface, relative to a plane formed by the X-ray beam and a normal to the two-dimensional X-ray detector. An angle φ is incremented for each of the measurements to provide the plurality of rotational orientations of the sample about $S_3$, while keeping the tilt angle ψ constant. This is to avoid the significant sample height error, to which low 2θ measurements are highly sensitive, associated to the movement of the cradle track with which the tilt angle ψ is maintained.

In conventional X-ray diffraction parlance, a "low" 2θ angle measurement is often considered to be one that is between 5° and 10°. In the present application, however, the term "relatively low angle" is used to describe a 2θ less than 90°, which is relevant in the context of the invention as it is low enough to cause significant sample height error in the context of a goniometer. Typically, the incident angle is half the angle 2θ, and would thus be considered as relatively low if it is less than 45°.

Performing X-ray diffraction measurements requires a number of measurements N for the X-ray diffraction stress analysis to be complete, and for each of the measurements, the angle φ is incremented by an increment Δφ, of which 360° is an integer multiple. The number of measurements N is 360°/Δφ.

In one embodiment of the invention, a location and a size of the detector relative to the sample and a nature of the sample determine a maximum tilt angle coverage required for the X-ray diffraction stress analysis. The tilt angle is about half the maximum tilt angle coverage. The two-dimensional detector is preferably positioned such that a detection surface of the detector is located substantially entirely to one side of a plane defined by an incident beam from the X-ray source and $S_3$, to avoid redundancy in collected data and reduce the number of measurements needed for stress tensor characterization.

In one particular embodiment of the invention, for each of the measurements, the angle φ is incremented by an increment Δφ=45°, the number of measurements is 8, and the tilt angle is about ψ=22.5°.

DETAILED DESCRIPTION

Figure 4:
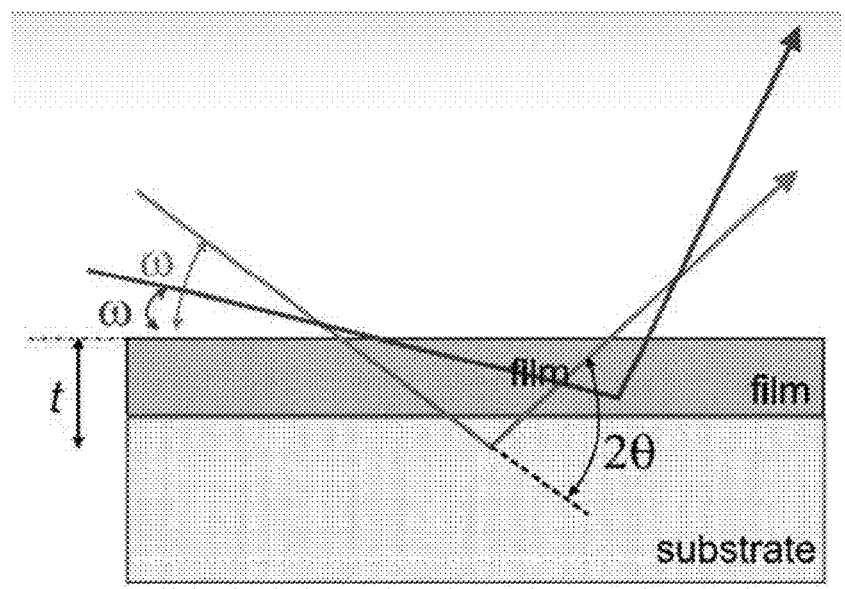
FIG. 4 is a side view of X-ray beams diffracted in a thin film sample with a variable penetration due to different incident angles.
Figure 5:
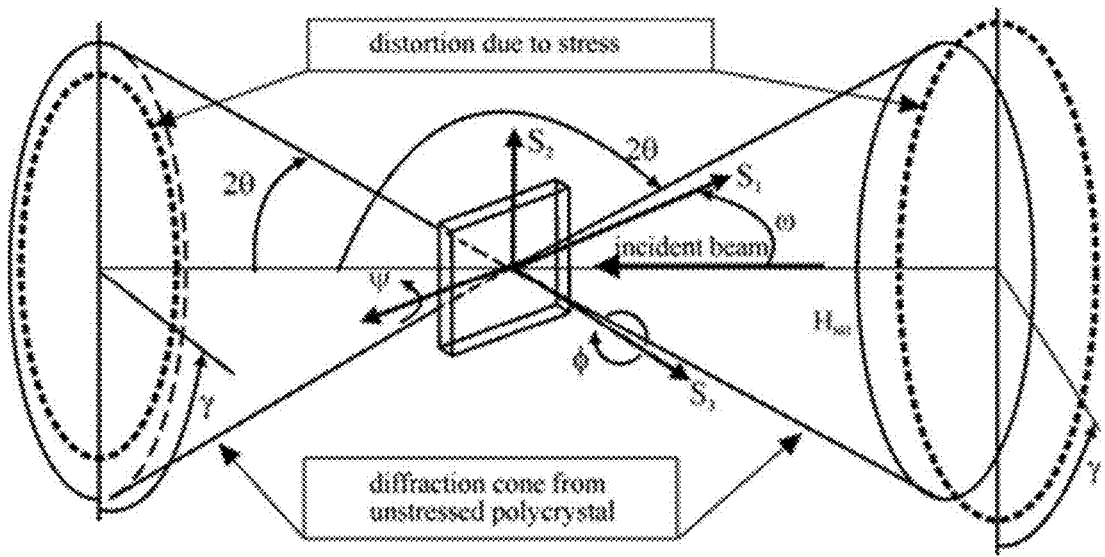
FIG. 5 is a schematic representation of X-ray diffraction cones at a shifted 2θ angle from a sample under stress.
Figure 6:
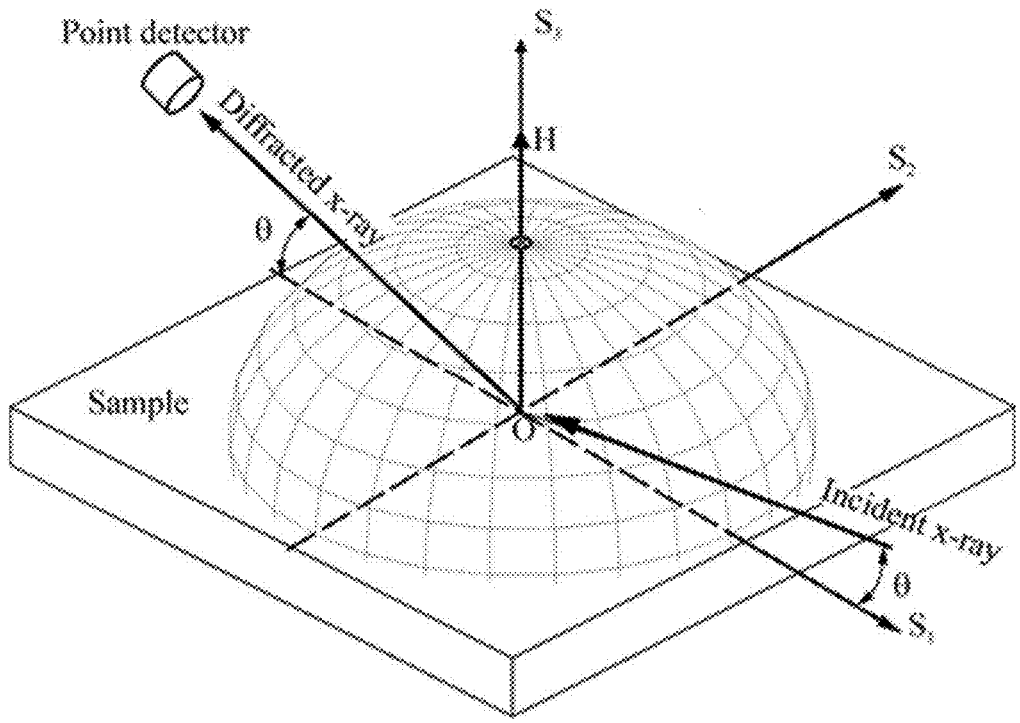
FIG. 6 is a schematic representation of a diffracted X-ray collected by a point detector with a tilt angle ψ=0° and a corresponding diffraction vector, according to the prior art.

Goniometers can achieve a precise location and orientation for the sample on the sample holder, but this precision is not perfect. In practice, the weight of the sample and of goniometer components and the often imperfect circular shape of the cradle track used to move the sample to different tilt angles ψ are among the most significant contributors to error. One notable error is the height error. In practice, when the sample is variably tilted by moving the sample holder on the cradle track, the location of the sample surface along the z-axis and the orientation of the sample surface change, and this change creates a shift on the diffraction angle 2θ measured on the detector, as shown in FIG. 4. This undesirable effect is strong for thin films and coatings, because a low incident angle is typically used for these types of samples.

One may consider detecting diffracted X-ray beams at a low 2θ angle if a low incident angle is used. However, for stress measurements, the stress-induced shift in 2θ for a given arc of a diffraction cone circle is proportional to 2θ. Therefore, stress measurements, in general, benefit from using high 2θ measurements: the shift being proportional to the high value of 2θ increases the sensitivity of the measurement, and the stress-induced shift in 2θ stands out better from the noise-induced shift in 2θ caused by the sample height error. High 2θ measurements are defined as those where the angle of diffraction 2θ is high enough, usually greater than 90°, to ensure the height error does not affect significantly the shift in 2θ compared to the stress-induced shift. The stress-induced shift is thus more accurately measured as it forms most of the total shift. If a low 2θ diffraction cone is used for the measurement, the relative contribution of noise-induced shift to the total shift is larger and stress-induced shift is thus less accurately measured. As such, low 2θ measurements for thin films and coatings are avoided in conventional methods. However, for many materials, especially coatings or thin films, high 2θ diffraction cones may not be available or appropriate for stress evaluation.

Figure 1:
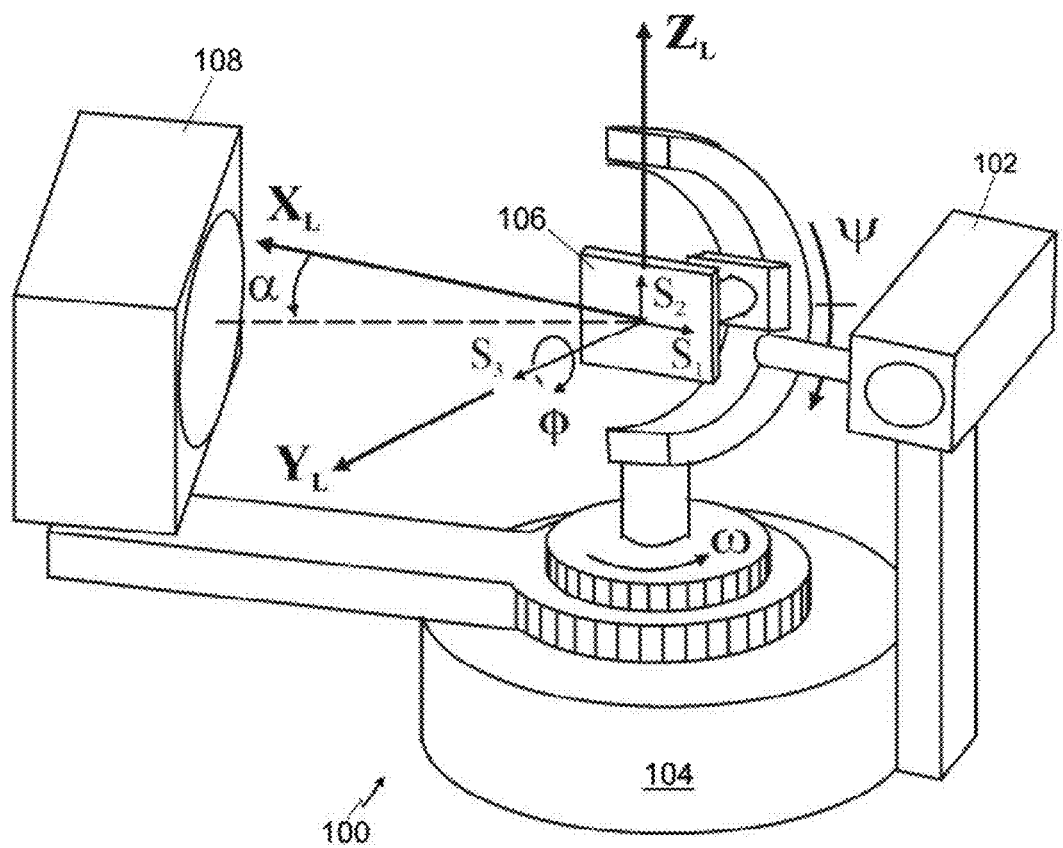
FIG. 1 is a perspective view of a goniometer having a cradle track holding the sample.
Figure 2:
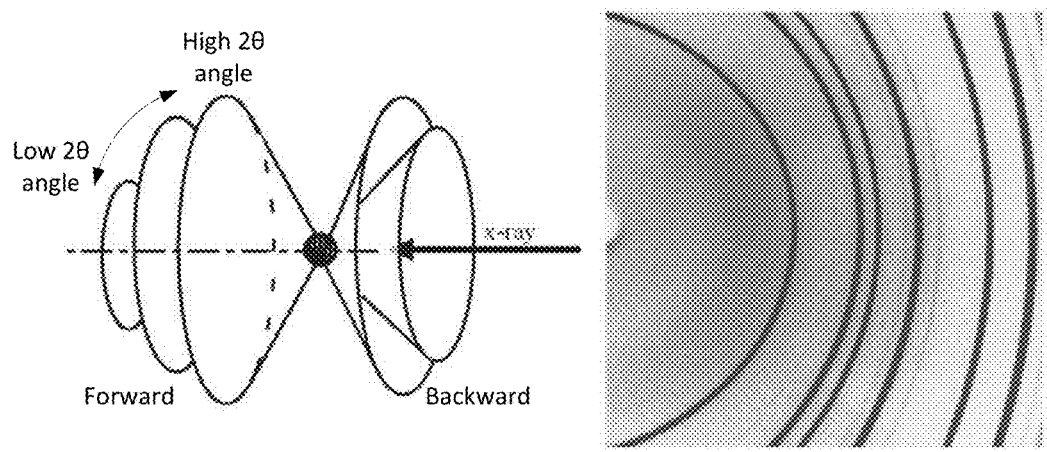
FIG. 2 is a schematic representation of diffraction cones and diffraction rings within which X-ray energy diffracted from a sample resides.
Figure 3:
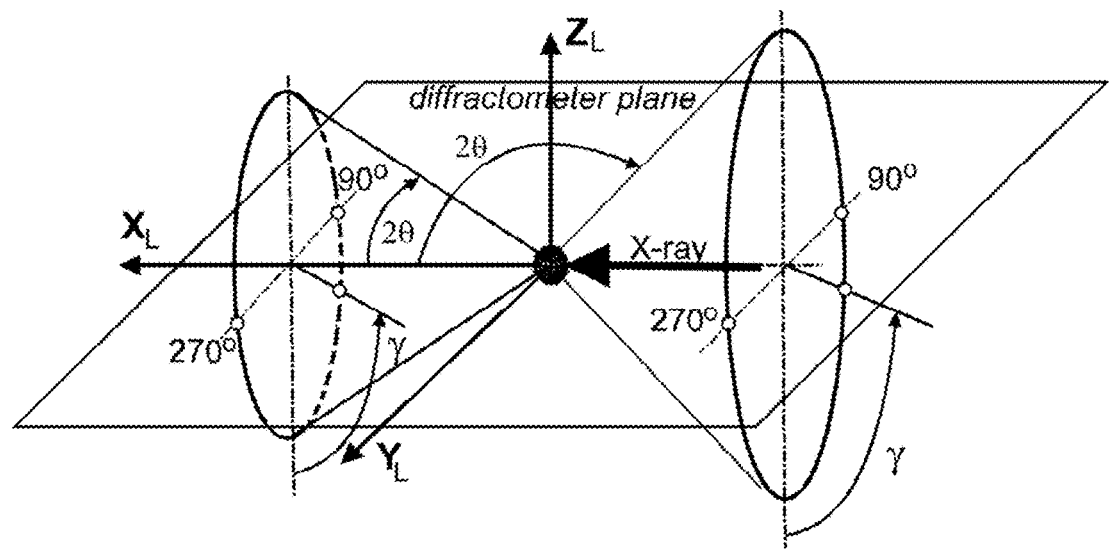
FIG. 3 is a schematic representation of a diffraction cone within which X-ray energy diffracted from a sample resides.

In conventional stress measurement systems, variation of the tilt angle ψ introduces a varying mechanical error in the sample height which in turn adds an error in the measured values. The tilt angle ψ is the angle of $S_3$, the normal to the sample surface, relative to a plane formed by the X-ray beam and a normal to the two-dimensional X-ray detector. With the present invention, the tilt angle $\psi$ is kept constant during the measurement, and the only angle changing during the measurement is $\phi$ (the angles being defined as shown in FIG. 1). Unlike changes to the tilt angle $\psi$, a rotation of the sample by an angle $\phi$ has little effect on the spherical error. Therefore, the stress can be more accurately determined in low $2\theta$ diffraction rings since the dominant varying shift in $2\theta$ is the stress-induced shift.

When stress is a measured by a diffractometer with a point detector or 2D detector with multiple tilt angles, the X-ray measurement instrument needs to be critically aligned in different axes to avoid mechanical error on sample height during sample rotation around these axes. However, the spherical error associated with the weight of heavy mechanical components and mechanical tolerance always exists. Building and maintaining an instrument with such a small mechanical error is costly and poses a challenge to the operator who has to recalibrate the goniometer repeatedly. Another challenge results from the fact that low $2\theta$ measurements are more sensitive than high $2\theta$ measurements to vertical misalignment. Generally, high $2\theta$ peaks are preferred for stress measurement in crystals due to the more significant $2\theta$ shift and lesser sensitivity to the sample height error. The shift in the value of $2\theta$ is proportional to $2\theta$ and thus results in a greater absolute shift that can be accurately measured. But for thin films, coatings, or polymer materials, high $2\theta$ peaks may not be available or appropriate for stress measurement. With low $2\theta$ peaks, it is more difficult or even impossible to measure stress with the conventional methods, and the measurement results of these the conventional methods are extremely sensitive to the sample height error.

The term "low $2\theta$" should be viewed in the context of the present invention, since in other applications outside of the context of the invention, the $2\theta$ angle may not be considered as low even though it is under 90°. The measurements with relatively low $2\theta$ angles are intended to encompass those angles under 90° for which there is significant sample height error. Furthermore, the incident angle of the X-ray beam may be as large as the $2\theta$ angle but is typically half the $2\theta$ angle, and if both angles have an exemplary value of 30°, the incident angle of 30° will not be considered as "low" in many X-ray applications. However, the $2\theta$ angle of 30° is considered as relatively "low" in the present context because significant sample height error is usually present at this $2\theta$ angle. Since the incident angle of the X-ray is typically half the $2\theta$ angle, it should be considered "relatively low" if it less than 45°.

There is disclosed below a device, more precisely a diffractometer with a 2D detector, and a method to operate the device to measure stress with a single sample tilt angle $\psi$ using low $2\theta$ measurements.

With two-dimensional X-ray diffraction, i.e., using a 2D detector, stress measurement is based on a direct relationship between a stress tensor and a degree of distortion in a measured diffraction cone that results therefrom. The fundamental equation for stress measurement is developed with the matrix transformation defined for the two-dimensional diffraction. For each single measurement, the diffraction vectors cover a wide range of directions and sufficient angular coverage can be achieved with a single tilt angle $\psi$ during the entire stress measurement. Therefore, the data collection is performed at a fixed $\psi$ angle with only $\phi$ rotation, if needed, as described more thoroughly below.

Figure 9:
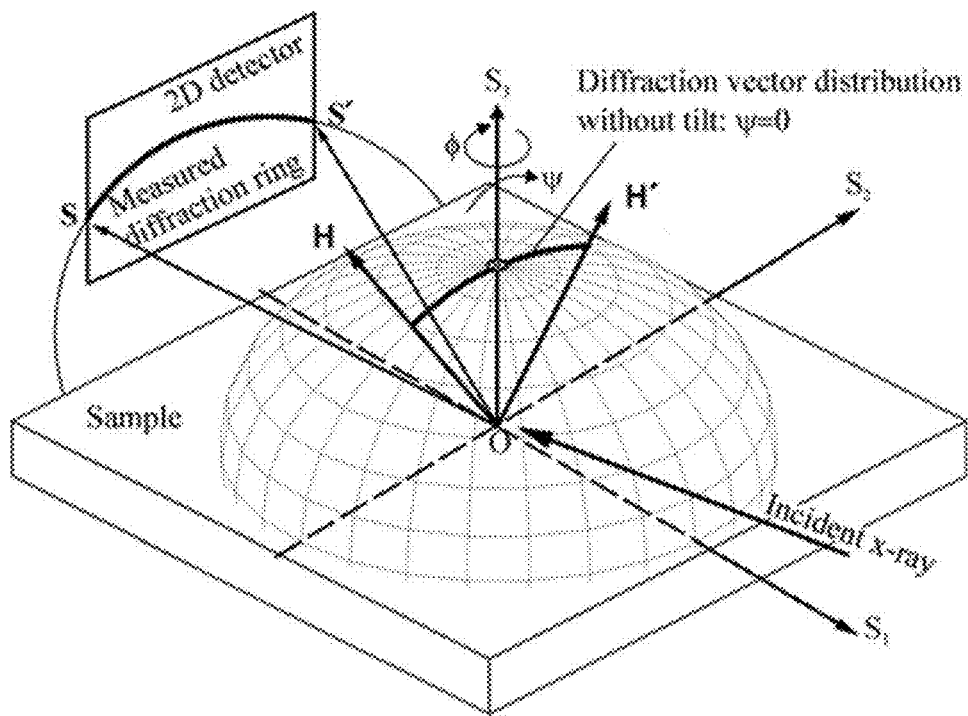
FIG. 9 is a schematic representation of a portion of a diffraction ring collected by a 2D detector and a corresponding diffraction vector distribution with a tilt angle ψ=0°, according to an embodiment of the invention.

FIG. 9 illustrates the diffraction vector coverage of the diffraction pattern collected with a 2D detector. The diffraction vector trace on the hemisphere is equally distributed on both sides of the sample normal $S_3$. Based on Equation (3), the range of this coverage is determined by both the $2\theta$ angle and the angular coverage of the detector, $\Delta\gamma$. The value of $2\theta$ is determined by the crystal structure of the material and the wavelength of the X-ray beam. $\Delta\gamma$ is determined by the size of the detector and the sample-to-detector distance. Since the sample can be rotated to be at various $\phi$ angles, the redundancy of the diffraction vector coverage above the sample normal direction is not necessary. In order to expand the diffraction vector coverage, the sample can be tilted to an angle $\psi \neq 0°$.

Figure 10:
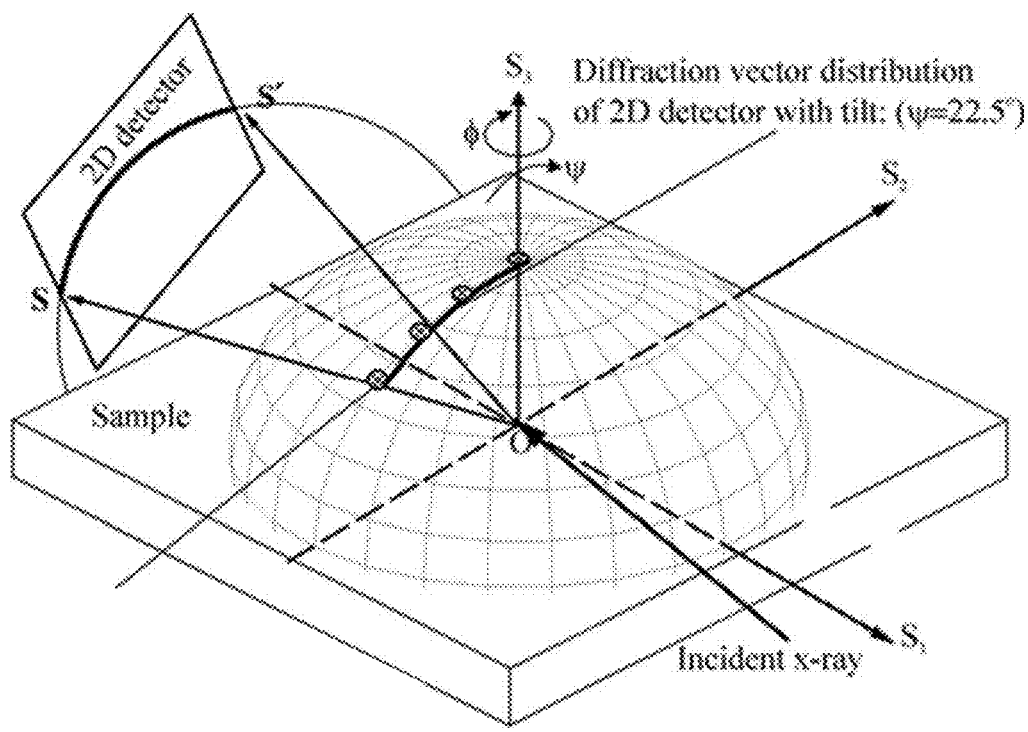
FIG. 10 is a schematic representation of a portion of a diffraction ring collected by a 2D detector at a tilt angle ψ=22.5°, and a corresponding diffraction vector distribution covered thereby.

FIG. 10 shows the diffraction vector distribution with a single tilt angle $\psi \neq 0°$. For instance, with a tilt angle of $\psi=22.5°$, the diffraction vector covers a range similar to the four diffraction vector orientations for a 0D detector with $\psi$ taking the following values: 0°, 15°, 30° and 45° (shown in FIG. 10 for comparison). For low $2\theta$ diffraction rings at proper detector distance, it is possible to cover sufficient angular range for stress evaluation with a single tilt angle. The complete data set for the stress tensor can be collected at several $\phi$ angles, for instance by performing a 360° scan with 45° steps. Therefore, the complete data set is collected by scanning along a plurality of $\phi$ values (i.e., varying $\phi$, preferably with different discrete values along a range) while maintaining a fixed $\psi$ angle. The plurality of rotational orientations (i.e., $\phi$) are provided by rotating the sample about $S_3$, which is the direction normal to the $S_1 S_2$ plane forming the sample surface. The direction of $S_3$ varies with the tilt angle and is therefore kept constant during the measurements of the entire X-ray diffraction stress analysis.

The tilt angle $\psi$ can be chosen to maximize coverage for determining the trace of diffraction vectors. In the embodiment of FIG. 10, the tilt angle is chosen to allow measurement of diffraction angles corresponding to diffraction vectors ranging from the normal to the sample (e.g., $H_0$) to the diffraction vector that is angularly the most distant from the normal while still allowing detection by the detector. In an exemplary embodiment of the invention, the diffraction vector that is angularly the most distant from the normal forms an angle of 45° with the normal. As such, a tilt angle $\psi$ of is chosen to be 22.5° is used, which represents half of the maximum angle. Equation (3), depending on $\theta$ and $\Delta\gamma$, can be applied to determine this maximum range. Therefore, for a given measurement, and depending on the sample and the physical characteristics of the detector and the goniometer, the maximum value of the diffraction vector with respect to the normal from the sample surface may be determined.

Avoiding changes in the tilt angle can significantly reduce the sample height variation during the data collection, improving the accuracy of measurements as the sample height error is minimized and kept constant. The constant error implies that there is no variable error-induced shift in $2\theta$ that could be confused with the stress-induced one (both being combined into the total shift that is actually measured).

The diffraction vector is in the normal direction of the measured crystalline planes. The stress components within the sample surface plane are calculated using the elasticity theory from the measured strain in other directions. The final stress measurement results can be considered as an extrapolation from the measured values. The trace of diffraction vectors shown in FIG. 10 follows a single curve on the hemisphere that is transverse to the diffraction vectors that extend in the longitudinal direction from the origin O and pointing to the hemisphere where the trace is formed. In order to get more precise stress or stress tensor results, ϕ rotation is necessary to expand the coverage.

The ϕ rotation is performed by incrementing the value of ϕ by an increment Δϕ between each measurement. This increment between measurements needs to be added between measurements N times. Preferably, a complete set of measurements provides discrete increments of ϕ covering a 360° range. By selecting a value of the increment Δϕ where 360° is an integer multiple of Δϕ, the 360° range can be covered with N=360°/Δϕ measurements. For example, a value of Δϕ=45° can be selected, thereby requiring 8 measurements in total to cover the 360° range of ϕ values.

The complete measurement may also involve a smaller number of measurements if precision is not critical or if shearing stresses do not need to be measured. For example, it may be possible to perform a complete measurement with a single tilt angle and with a single value of ϕ. Using the equations of stress determination, the stress in one axis of the sample surface will be determined. By performing an additional measurement with the opposite value of ϕ (involving a 180° rotation from the initial value of ϕ), the stress in the same axis will be determined, but with greater accuracy as the 180° rotation of ϕ causes some error to cancel out. By performing an additional measurement in another value of ϕ involving a 90° rotation from the initial value of ϕ, the stress in the other axis of the sample surface will be determined. Optionally a 180° rotation of ϕ with respect to this second value of ϕ can also be performed to ensure greater accuracy in the stress determined along this other axis. If 45° increments of ϕ between measurements are chosen, shearing stresses can be determined. Again, the opposite value of ϕ can be used for each measurement to ensure greater accuracy in the determination of each stress component. Therefore, eight measurements using 45° increments of ϕ are sufficient to collect information for accurate stress determination for most tensor components of the stress.

Since the resulting diffraction vector distribution is symmetric on either side of the value ψ=0°, the portions of the two-dimensional detector that detect, respectively, diffracted X-ray energy to either side of the value ψ=0° will measure data giving the same information, albeit with greater accuracy overall. With the tilt angle chosen so that the trace of diffraction vectors determined to only one side of the normal to the sample, the angular coverage from the normal to the sample is maximized. For example, a trace of diffraction vectors covering an angular range from 0° from the normal to 45° provides data more useful for stress determination than a trace of diffraction vectors covering an angular range from −22.5° from the normal to +22.5°.

Figure 11:
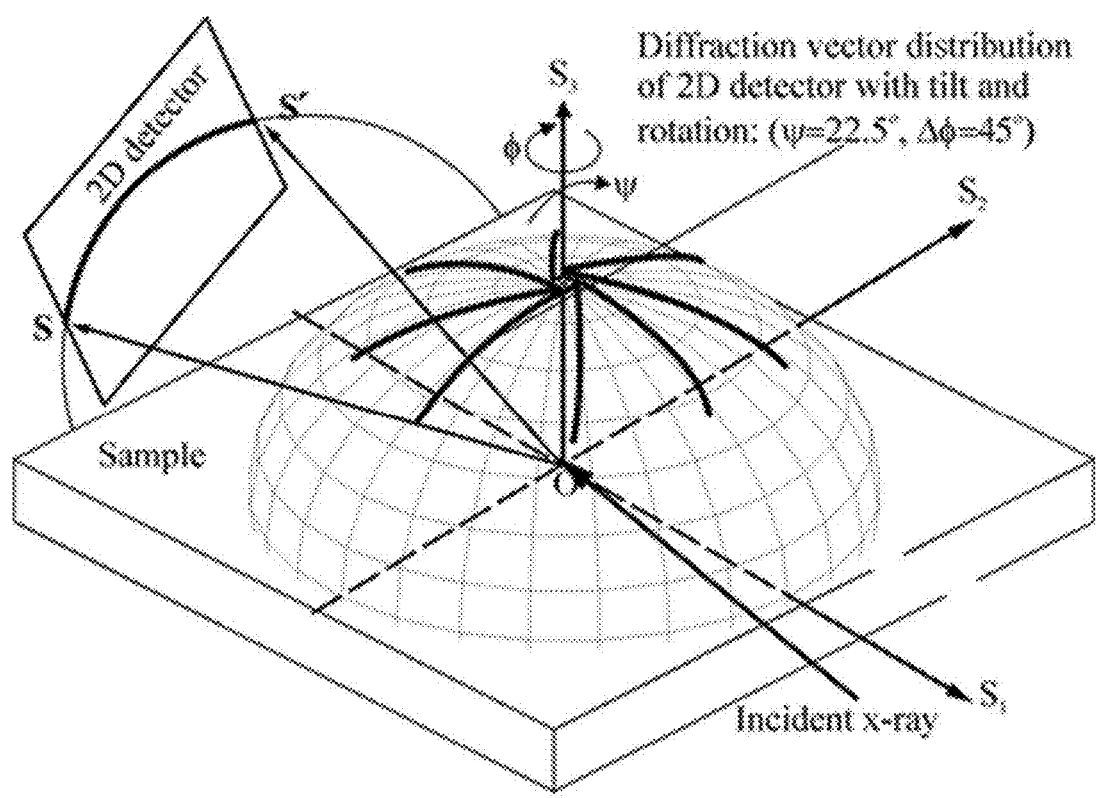
FIG. 11 is a schematic representation of diffraction vector traces collected using a tilt angle of ψ=22.5° and a complete φ rotation by 45° increments.

FIG. 11 illustrates a system arranged with a tilt angle of ψ=22.5° with eight different values of ϕ angles at 45° intervals. In this data collection scheme, eight frames are collected to produce a comprehensive coverage in a symmetric distribution. The data set collected with this strategy can be used to calculate the complete biaxial stress tensor components and shear stress ($\sigma_{11}$, $\sigma_{12}$, $\sigma_{22}$, $\sigma_{13}$, $\sigma_{23}$). As can be expected by a person skilled in the field, a different combination of ψ angle or number of ϕ angles and steps could also be chosen to achieve the desired angular coverage.

Figure 12:
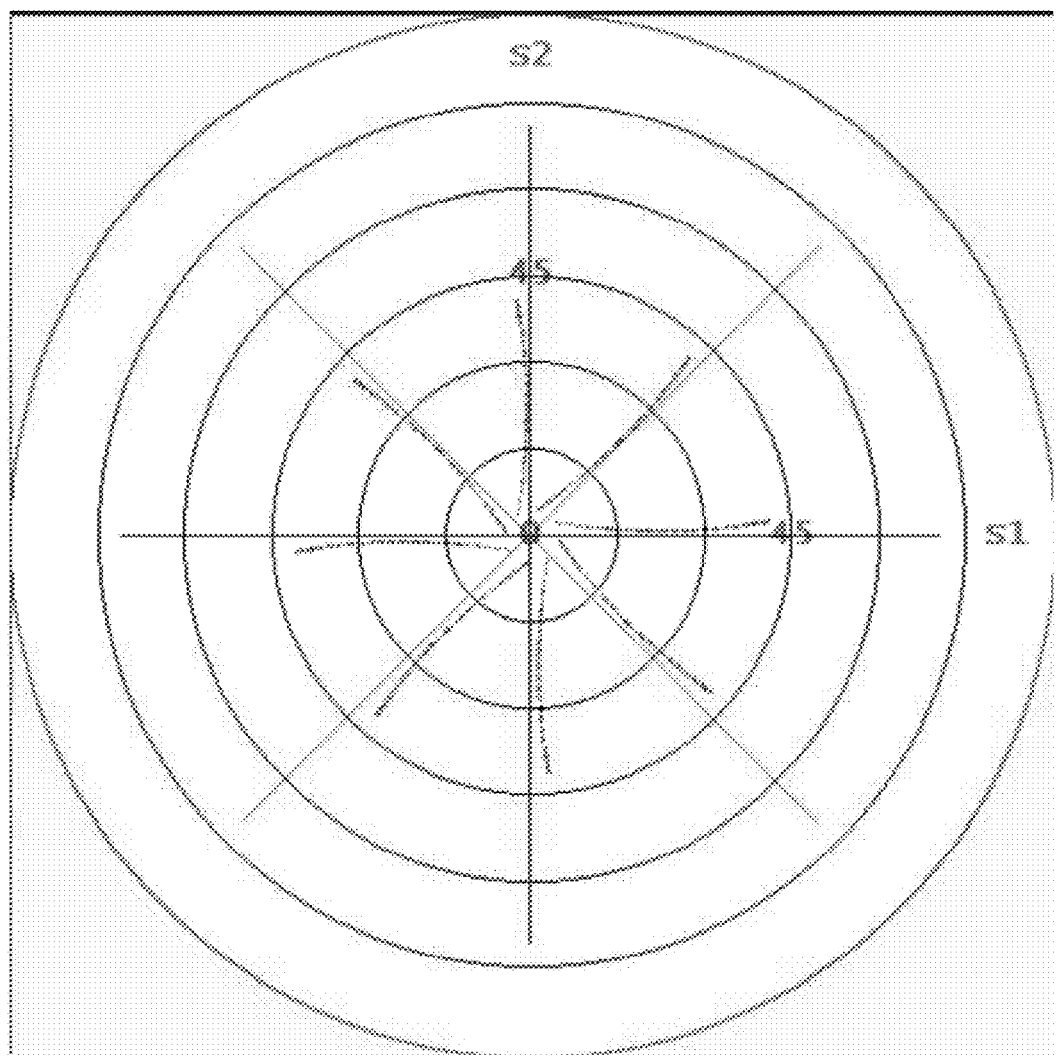
FIG. 12 is a graph of the results from the setting of FIG. 11, where the trace of diffraction vectors is projected on the sample surface plane.

Exemplary results of this measurement are shown in FIG. 12, which illustrates a projection on the $S_1 S_2$ plane of the continuously varying intersection points of the diffraction vector H along a spherical surface like those shown in previous figures. Each branch in the graph of FIG. 12 corresponds to all intersection points of the diffraction vector H with the sphere for a measurement with a given value of ϕ, that is, the eight branches correspond to the eight measurements with eight different values of ϕ.

These collected data can then be analyzed for the determination of the stress tensor. Maintaining the cradle track of the goniometer at a single value of the tilt angle during all measurements provides the necessary minimization of sample height error to be able to perform low 2θ measurements (those where the 2θ angle is low enough to cause significant sample height error) with high accuracy. Calibration time and efforts are also minimized. The number of measurements and duration of each measurement are thus reduced too.

Figure 7:
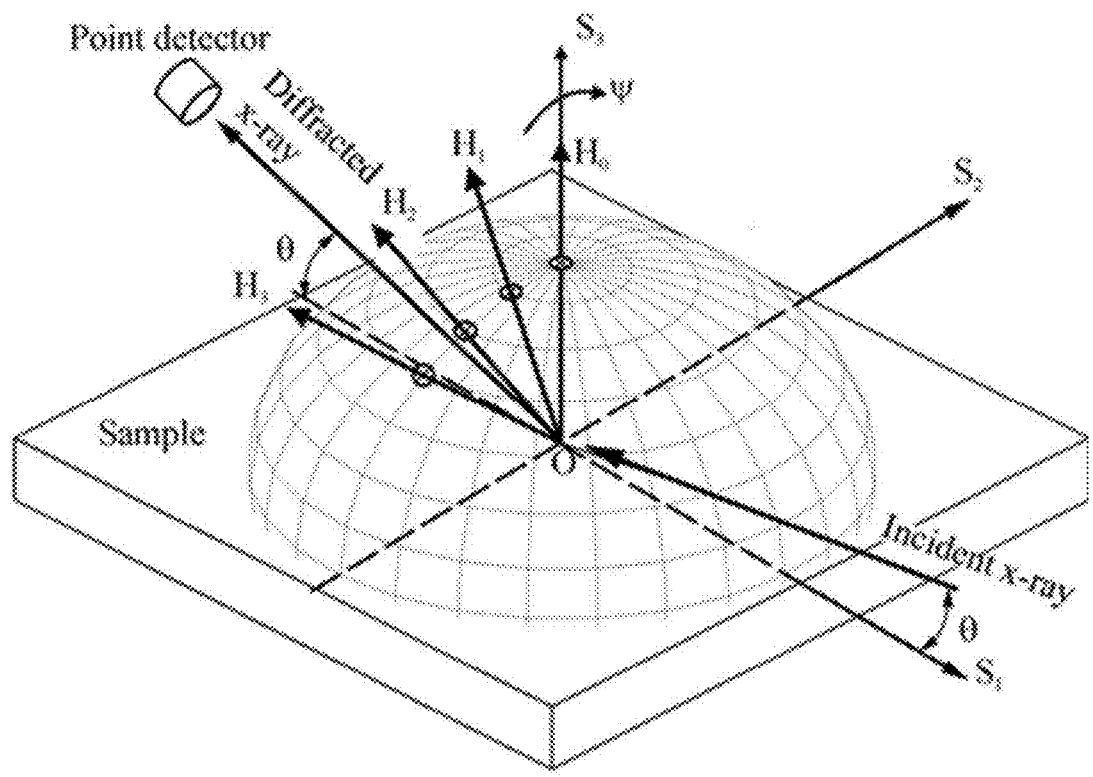
FIG. 7 is a schematic representation of a diffracted X-rays collected by a point detector with various tilt angles ψ and corresponding diffraction vectors, according to the prior art.
Figure 8:
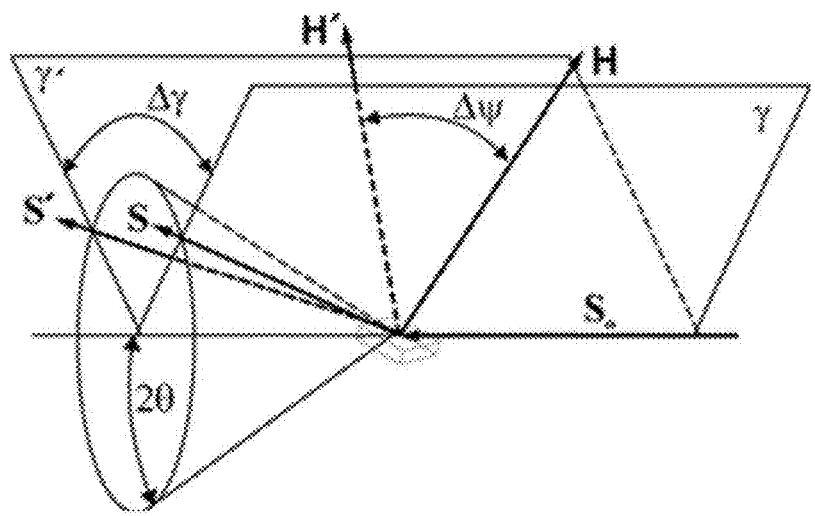
FIG. 8 is a schematic representation of an angle between two diffraction vectors with different γ values.

In contrast, with the present invention, prior art methods using point detector would require each branch in the graph to be determined by making four measurements ($H_0$ to $H_3$) which requires varying the tilt angle ψ each time, as shown in FIG. 7. Thus, to have a complete data set with eight branches for stress tensor determination, one would need to perform 32 measurements instead of 8 as in the present invention. The duration of the complete data set acquisition would thus be significantly longer and the final result would be less accurate due to errors introduced by varying the tilt angle ψ between each one of the 32 measurements.

For thin films, coatings, polymers or other polycrystalline materials, when the diffraction cones at high 2θ angles are not available or appropriate, a low 2θ measurement can be performed for stress evaluation. With diffraction rings at a low 2θ angle, the diffraction vector distribution can satisfy the angular coverage needed for stress measurement at a fixed tilt angle ψ. Without changes of the tilt angle ψ during data collection and with rotation along ϕ only, the sample height is accurately maintained. The error that would be introduced in the sample height by varying the tilt angle ψ is avoided and is not passed on to the accuracy of stress measurement. Therefore the single tilt method with a 2D detector system can measure residual stress with high accuracy and high speed for thin films, coatings and polymers.

While the invention has been shown and described with reference to specific embodiments thereof, it will be recognized that various changes in form and detail may be made herein without departing from the spirit and scope of the invention as defined by the appended claims.

The invention claimed is:

1. A method of performing an X-ray diffraction stress analysis of a sample having a surface with two perpendicular axes $S_1$, $S_2$ within a plane of the surface, a third axis $S_3$ being perpendicular to the sample surface plane, the method comprising directing an X-ray beam at the sample surface at a relatively low angle with regard to the surface plane and detecting, at a diffraction angle 2θ, X-ray energy diffracted from the sample with a two-dimensional X-ray detector at a plurality of rotational orientations of the sample about $S_3$, the third axis $S_3$ being maintained, during the entire X-ray diffraction stress analysis, at a constant tilt angle ψ relative to a plane formed by the X-ray beam and a normal to the two-dimensional X-ray detector.

2. The method of claim 1, wherein the sample is at least one of: a thin film, a coating, and a polymer.

3. The method of claim 2, wherein the diffraction angle is under 90°.

4. The method of claim 3, wherein performing the entire X-ray diffraction stress analysis requires a number of measurements N, wherein for each of the measurements at the plurality of rotational orientations of the sample about $S_3$ defined by an angle ϕ, the angle ϕ is incremented by an increment Δϕ.

5. The method of claim 4, wherein 360° is an integer multiple of $\Delta\phi$, and the number of measurements N is $360°/\Delta\phi$.

6. The method of claim 5, wherein for each of the measurements, the angle $\phi$ is incremented by an increment $\Delta\phi=45°$.

7. The method of claim 1, wherein the tilt angle is selected such that a detection surface of the detector is located substantially entirely to one side of a plane defined by an incident beam from the X-ray source and $S_3$.

8. The method of claim 7, wherein the tilt angle is selected based on an angular range, $\Delta\gamma$, of diffracted X-ray energy that is detectable by the detector.

9. The method of claim 8, wherein the tilt angle is about half of said angular range.

10. The method of claim 9, wherein maintaining the third axis $S_3$ at a constant tilt angle comprises using a cradle track holding the sample and maintaining the cradle track at the tilt angle during the entire X-ray diffraction stress analysis.

11. The method of claim 1, wherein directing an X-ray beam at the sample surface at a plurality of rotational orientations of the sample about $S_3$ is performed using a goniometer to hold and rotate the sample.

12. The method of claim 1, wherein the relatively low angle with regard to the surface plane is less than 45°.

13. An apparatus for performing an X-ray diffraction stress analysis of a sample having a surface with two perpendicular axes $S_1$, $S_2$ within a plane of the surface, a third axis $S_3$ being perpendicular to the sample surface plane, the apparatus comprising:
a sample holder for holding the sample, the sample holder being orientable at a plurality of rotational orientations of the sample about $S_3$;
an X-ray source producing an X-ray beam and directing the X-ray beam at the sample surface at a relatively low angle with regard to the surface plane; and
a two-dimensional X-ray detector detecting, at a diffraction angle 2θ, X-ray energy diffracted from the sample at the plurality of rotational orientations of the sample about $S_3$, the third axis $S_3$ being maintained, during the entire X-ray diffraction stress analysis, at a constant tilt angle $\psi$ relative to a plane formed by the X-ray beam and a normal to the two-dimensional X-ray detector.

14. The apparatus of claim 13, wherein the sample is at least one of: a thin film, a coating, and a polymer.

15. The apparatus of claim 14, wherein the diffraction angle is under 90°.

16. The apparatus of claim 13, further comprising a goniometer to orient the sample holder.

17. The apparatus of claim 16, wherein the goniometer comprises a cradle track holding the sample holder, the cradle track being maintainable at the tilt angle during the entire X-ray diffraction stress analysis.

18. The apparatus of claim 13, wherein the tilt angle is selected such that a detection surface of the detector is located substantially entirely to one side of a plane defined by an incident beam from the X-ray source and $S_3$.

19. The apparatus of claim 18, wherein the tilt angle is selected based on an angular range, $\Delta\gamma$, of diffracted X-ray energy that is detectable by the detector.

20. The apparatus of claim 19 wherein the tilt angle is about half of said angular range.

21. The apparatus of claim 13, wherein the entire X-ray diffraction stress analysis requires a number of measurements N, wherein for each of the measurements at the plurality of rotational orientations of the sample about $S_3$ defined by an angle $\phi$, the angle $\phi$ is incremented by an increment $\Delta\phi$.

22. The apparatus of claim 21, wherein 360° is an integer multiple of $\Delta\phi$, and the number of measurements N is $360°/\Delta\phi$.

23. The apparatus of claim 22, wherein for each of the measurements, the angle $\phi$ is incremented by an increment $\Delta\phi=45°$.

* * * * *